US011748598B2

(12) United States Patent
Bai et al.

(10) Patent No.: US 11,748,598 B2
(45) Date of Patent: Sep. 5, 2023

(54) POSITRON EMISSION TOMOGRAPHY (PET) SYSTEM DESIGN OPTIMIZATION USING DEEP IMAGING

(71) Applicant: KONINKLIJKE PHILIPS N.V., Eindhoven (NL)

(72) Inventors: Chuanyong Bai, Solon, OH (US); Yang-Ming Zhu, Wilmington, MA (US); Andriy Andreyev, Willoughby Hills, OH (US); Bin Zhang, Cleveland, OH (US); Chi-Hua Tung, Aurora, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 252 days.

(21) Appl. No.: 16/758,000

(22) PCT Filed: Oct. 16, 2018

(86) PCT No.: PCT/EP2018/078126
§ 371 (c)(1),
(2) Date: Apr. 21, 2020

(87) PCT Pub. No.: WO2019/081256
PCT Pub. Date: May 2, 2019

(65) Prior Publication Data
US 2020/0289077 A1    Sep. 17, 2020

Related U.S. Application Data

(60) Provisional application No. 62/575,547, filed on Oct. 23, 2017.

(51) Int. Cl.
*A61B 6/00* (2006.01)
*A61B 6/03* (2006.01)
(Continued)

(52) U.S. Cl.
CPC ............ *A61B 6/5205* (2013.01); *A61B 6/037* (2013.01); *A61B 6/5235* (2013.01); *A61B 6/584* (2013.01); *G06N 3/045* (2023.01); *G06N 3/084* (2013.01)

(58) Field of Classification Search
None
See application file for complete search history.

(56) References Cited

U.S. PATENT DOCUMENTS 8,620,404 B2 * 12/2013 Mistretta ................. A61B 5/004
382/128
11,304,604 B2 * 4/2022 DiMaio ................... A61B 5/445
(Continued)

FOREIGN PATENT DOCUMENTS

| WO | 2016033458 A1 | 3/2016 |
| WO | 2016092394 A1 | 6/2016 |
| WO | 2018183044 A1 | 10/2018 |

OTHER PUBLICATIONS

Doroud K, Rodriguez A, Williams MC, Zichichi A, Zuyeuski R. Comparative timing measurements of LYSO and LFS to achieve the best time resolution for TOF-PET. In2014 IEEE Nuclear Science Symposium and Medical Imaging Conference (NSS/MIC) Nov. 8, 2014 (pp. 1-4). IEEE. (Year: 2014).*

(Continued)

*Primary Examiner* — Michelle M Entezari

(57) ABSTRACT

An imaging method (100) includes: acquiring first training images of one or more imaging subjects using a first image acquisition device (12); acquiring second training images of the same one or more imaging subjects as the first training images using a second image acquisition device (14) of the same imaging modality as the first imaging device; and training a neural network (NN) (16) to transform the first training images into transformed first training images having a minimized value of a difference metric comparing the (Continued)

transformed first training images and the second training images.

15 Claims, 2 Drawing Sheets

(51) Int. Cl.
*G06N 3/084* (2023.01)
*G06N 3/045* (2023.01)

(56) References Cited

U.S. PATENT DOCUMENTS

| | | | | |
|---|---|---|---|---|
| 2003/0235332 | A1* | 12/2003 | Moustafa | G06V 10/242 382/157 |
| 2006/0266947 | A1* | 11/2006 | Krieg | A61B 6/037 250/363.04 |
| 2011/0309256 | A1 | 12/2011 | Moriyasu | |
| 2012/0278034 | A1* | 11/2012 | Dong | G01T 1/2985 702/152 |
| 2013/0051516 | A1 | 2/2013 | Yang | |
| 2014/0061483 | A1 | 3/2014 | Yoshida | |
| 2015/0112182 | A1 | 4/2015 | Sharma | |
| 2015/0201895 | A1 | 7/2015 | Suzuki | |
| 2016/0093048 | A1 | 3/2016 | Cheng | |
| 2016/0210749 | A1* | 7/2016 | Nguyen | G06N 3/0454 |
| 2016/0331341 | A1* | 11/2016 | Brendel | G06T 7/215 |
| 2017/0103512 | A1 | 4/2017 | Maihe | |
| 2018/0018757 | A1* | 1/2018 | Suzuki | G06T 3/4053 |
| 2018/0060512 | A1* | 3/2018 | Sorenson | G16H 30/40 |
| 2018/0197106 | A1* | 7/2018 | Fujitani | G06N 20/00 |
| 2018/0198800 | A1* | 7/2018 | Krasser | G06N 20/00 |
| 2018/0330233 | A1* | 11/2018 | Rui | G06N 3/084 |
| 2019/0192880 | A1* | 6/2019 | Hibbard | A61N 5/1039 |
| 2020/0222119 | A1* | 7/2020 | Kruecker | G16H 50/30 |

OTHER PUBLICATIONS

Du J, Wang Y, Zhang L, Zhou Z, Xu Z, Wang X. Physical properties of LYSO scintillator for NN-PET detectors. In2009 2nd International Conference on Biomedical Engineering and Informatics Oct. 17, 2009 (pp. 1-5). IEEE. (Year: 2009).*

Clement, Christoph, et al. "Deep Learning for Predicting Gamma-Ray Interaction Positions in LYSO Detector." 2021 43rd Annual International Conference of the IEEE Engineering in Medicine & Biology Society (EMBC). IEEE, 2021. (Year: 2021).*

Gong K, Berg E, Cherry SR, Qi J. Machine learning in PET: from photon detection to quantitative image reconstruction. Proceedings of the IEEE. Sep. 19, 2019;108(1):51-68. (Year: 2019).*

Mehranian, Abolfazl, et al. "Image enhancement of whole-body oncology [18F]-FDG PET scans using deep neural networks to reduce noise." European journal of nuclear medicine and molecular imaging 49.2 (2022): 539-549. (Year: 2022).*

Schaart, Dennis R., et al. "Time of flight in perspective: instrumental and computational aspects of time resolution in positron emission tomography." IEEE transactions on radiation and plasma medical sciences 5.5 (2021): 598-618. (Year: 2021).*

International Search Report and Written Opinion of PCT/EP2018/078126, dated Jan. 31, 2019.

Wang, GE "A Prospective on Deep Imaging", Digital Object Identifier 10.1109, Nov. 3, 2016.

"Computers Trounce Pathologiest in Predicting Lung Cancer Type, Severity, Researchers find", Aug. 16, 2016, Science Daily, Stanford University Medical Center.

"Artificial Intelligence Achieves Near-Human Performance in Diagnosing Breast Cancer", Jun. 20, 2016. Science Daily, Beth Israel Deaconess Medical Center.

Dong, Chao et al. "Image Super-Resolution using Deep Convolutional Networks", IEEE Transactions on Attern Analysis and Machine Intelligence, vol. 38, No. 2, Feb. 2016.

* cited by examiner

POSITRON EMISSION TOMOGRAPHY (PET) SYSTEM DESIGN OPTIMIZATION USING DEEP IMAGING

CROSS-REFERENCE TO PRIOR APPLICATIONS

This application is the U.S. National Phase application under 35 U.S.C. § 371 of International Application No. PCT/EP2018/078126, filed on Oct. 16, 2018, which claims the benefit of U.S. Provisional Patent Application No. 62/575,547, filed on Oct. 23, 2017. These applications are hereby incorporated by reference herein.

FIELD

The following relates generally to the medical imaging arts, medical image interpretation arts, image reconstruction arts, deep learning arts, and related arts.

BACKGROUND

High-end Positron Emission Tomography/ComputedTomography (PET/CT) systems use advanced techniques in hardware design, such as digital detection techniques, high timing resolution time of flight (TOF) electronics, as well as advanced data processing software, such as list-mode TOF reconstruction. The main drawbacks are the associated system complexity, design and manufacturing cost, maintenance cost, etc.

Cost reduction by optimizing the system design while preserving the system performance for clinical applications is one of the biggest industrial challenges to PET/CT systems. One major effort for cost reduction is to use less expensive crystals, since crystal cost is a substantial component of the total cost for a PET system. However, reducing the cost of crystals is almost always associated with performance compromise. For example, using a less-expensive crystal as compared to a Lutetium-yttrium oxyorthosilicate (LYSO) crystal may reduce the overall PET/CT system cost, but one may only be able to achieve a suboptimal TOF resolution.

Software approaches have been developed to improve the performance of systems with low cost, mostly through advanced reconstruction and data processing algorithms. For example, some existing reconstruction software programs can be used to improve the image quality from systems with low-resolution TOF or systems without TOF capability at all. Improvement from such conventional reconstruction and data processing algorithms may not be enough to bridge the gap between the system performance and customer needs.

PET/CT design optimization is a balance of desired system performance and cost (life cycle cost that includes manufacturing cost, operating and maintenance cost, etc.). Low-end PET/CT systems have lower cost, but performance can be compromised. Conventional software solutions can improve the performance (image quality, quantitation, etc.) of low-end system, but often not enough to improve the performance to the satisfactory level.

The following discloses new and improved systems and methods to overcome these problems.

SUMMARY

In one disclosed aspect, an imaging method includes: acquiring first training images of one or more imaging subjects using a first image acquisition device; acquiring second training images of the same one or more imaging subjects as the first training images using a second image acquisition device of the same imaging modality as the first imaging device; and training a neural network (NN) to transform the first training images into transformed first training images having a minimized value of a difference metric comparing the transformed first training images and the second training images.

In another disclosed aspect, a non-transitory computer-readable medium stores instructions readable and executable by at least one electronic processor to perform an imaging method including: acquiring a subject image of a subject using a first image acquisition device; applying a trained neural network to the subject image to generate a transformed subject image; and displaying the transformed subject image. The trained neural network is configured by neural network training to transform first training images acquired of one or more training subjects by the first image acquisition device or by an equivalent image acquisition device into transformed first training images for which a value of a difference metric comparing the transformed first training images and second training images acquired of the one or more training subjects by a second image acquisition device that is not equivalent to the first imaging device is minimized by the training.

In another disclosed aspect, an imaging system includes a first image acquisition device configured to acquire imaging data of a subject. At least one electronic processor is programmed to: process the imaging data to generate a transformed subject image by one of (i) reconstructing the imaging data to generate a reconstructed image and applying an image domain trained neural network to the reconstructed image or (ii) applying a trained imaging data domain neural network to the imaging data to generate transformed imaging data and reconstructing the transformed imaging data; and control a display device to display the transformed subject image. One of: (ia) the trained image domain neural network is configured by neural network training to transform first training images acquired of one or more training subjects by the first image acquisition device into transformed first training images for which a value of a difference metric comparing the transformed first training images and second training images acquired of the one or more training subjects by a second image acquisition device is minimized by the training, or (iia) the trained imaging data domain neural network is configured by neural network training to transform first training imaging data acquired of one or more training subjects by the first image acquisition device into transformed first training imaging data for which a value of a difference metric comparing the transformed first training imaging data and second training imaging data acquired of the one or more training subjects by the second imaging device is minimized by the training.

One advantage resides in using deep learning to program a lower-end imaging system to produce images comparable with those of a higher-end imaging system.

Another advantage resides in providing a PET/CT system that uses deep imaging approach with data from high-end PET/CT systems for the design optimization of low-end PET/CT systems.

Another advantage resides in providing a low-end PET/CT imaging system trained with deep imaging data sets from high-end PET/CT imaging systems with low-end imaging data and high-end imaging data, and applying the resultant deep imaging to the daily imaging process of the images to low-end systems.

Another advantage resides in combining datasets from both high- and low-end systems to jointly train the deep imaging neural network to further improve the image from the low-end systems and their clinical usage (including feature identification, quantitation improvement).

Another advantage resides in reduced cost for a medical facility by purchasing a low-end imaging system trained with data from a high end imaging system.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
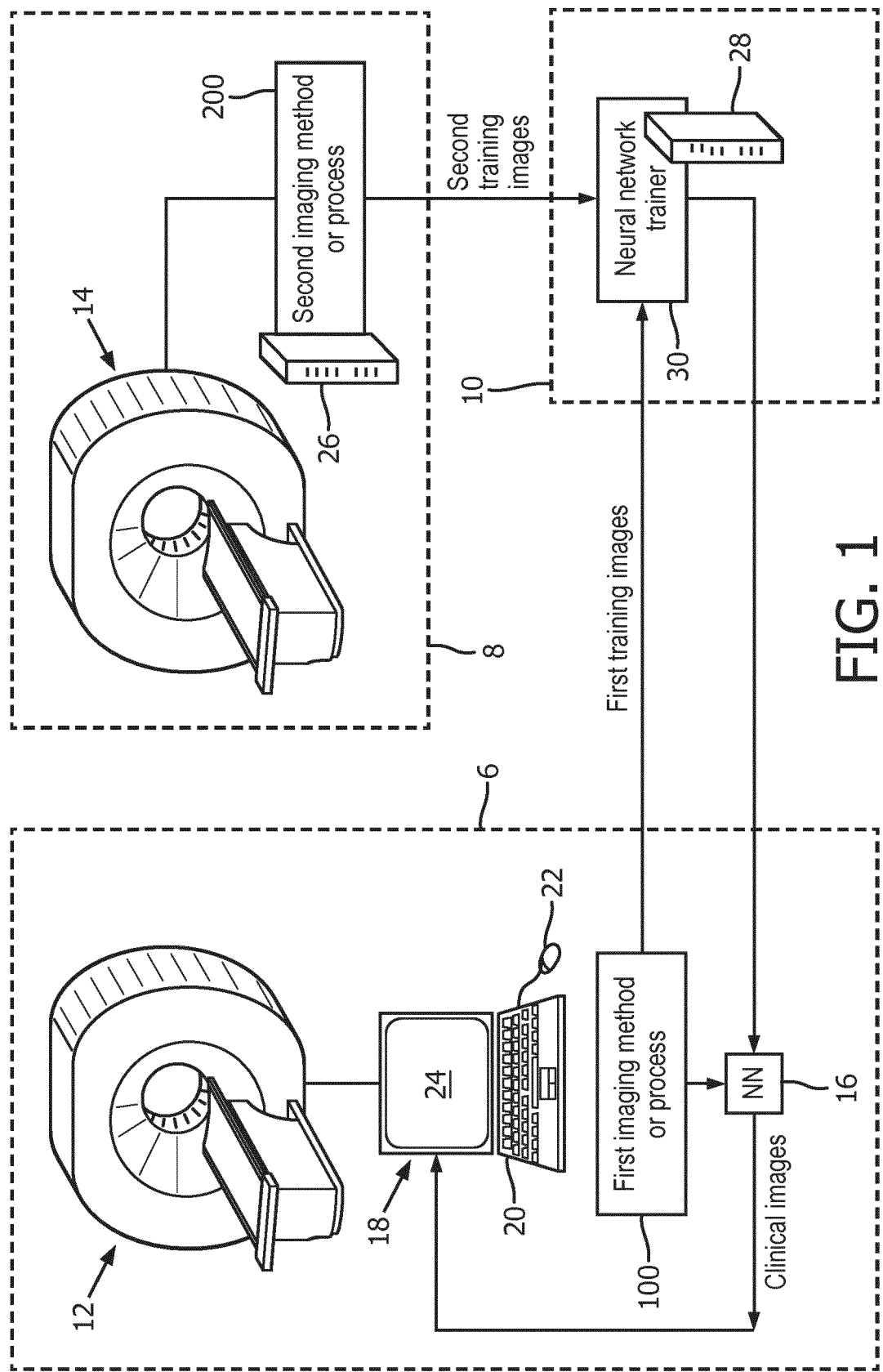
FIG. 1 diagrammatically shows an imaging system according to one aspect.

PET system product lines from commercial vendors typically include models ranging from "entry level" to "premium". The entry level systems are usually non-TOF, i.e. do not acquire or leverage information on time-of-flight localization of events along respective lines-of-response (LORs), and use larger-sized detector scintillator crystals leading to substantially lower resolution; whereas, the premium systems acquire TOF localization information along the LORs and leverage this information in the image reconstruction and use smaller, faster scintillator crystals and improved image processing to provide images with better resolution and overall better image quality.

Premium PET systems are typically purchased and operated by medical institutions with extensive resources, and which employ personnel with extensive training available at such institutions, which further increases the divide between image quality obtained by these premium PET systems compared with entry level systems.

This gulf between premium and entry level system deployments cannot be remedied by upgrading the hardware of entry level systems, because such hardware upgrades would be costly and would thereby negate the ability to sell entry level PET systems at an entry level price point.

In general, software improvements on the processing side are more likely to be cost-effective for bridging the gap between entry level systems and premium systems, since hardware upgrades are generally more expensive. However, a substantial difficulty arises as the performance differences between premium and entry-level to be mitigated are difficult to isolate and quantify. Differences can be due to hardware differences, differences in workflows, differences in maintenance procedures, and/or so forth, and these various differences may or may not be amenable to mitigation by improved processing. Differences on the processing side can be differences in kind, e.g. non-TOF versus TOF reconstruction, or can be more subtle differences due to choices of filters, or filter parameters, used during the reconstruction. Furthermore, the resulting differences in images that translate to improved "image quality" can be similarly ill-defined.

The following discloses leveraging images acquired using a premium PET imaging system to improve image quality for entry level PET imaging systems. The disclosed approach is expected to improve mid-level or entry level PET imaging systems mitigating differences between the images produced by such systems compared with images produced by premium PET imaging systems.

The disclosed approach is to provide a deep learning component designed to transform images acquired by the entry level PET system into images more comparable with equivalent images acquired by a premium PET imaging system. To construct this component, first and second images of the same subject (human or phantom) are acquired using the entry level PET system (first system) and the premium PET system (second system), respectively, under equivalent conditions (e.g. same radiopharmaceutical, same time interval between agent administration and imaging, same imaged volume, same image acquisition time, et cetera). This can be repeated for a number of similar subjects, similar imaging scenarios, and so forth, to develop a training set of (first image, second image) pairs where each first image is acquired by the entry level PET system and each second image is acquired using the premium PET system.

The goal is then to train a deep learning component to transform each first image into a transformed first image that is as similar as feasible to the corresponding second image. Thereafter, the trained deep learning component is applied to clinical images acquired by the entry level PET system to transform them into images more similar to that which would be obtained using the premium PET system.

In embodiments disclosed herein, the deep learning component is a convolutional neural network (CNN) whose weights are trained to transform the first images acquired by the entry level PET system into transformed first images with minimum loss, where the loss is a metric quantifying the differences between the transformed first images and the corresponding second images. In general, the loss for each sample (i.e., each first/second image pair) is computed by spatially registering the transformed first image and the second image and then computing a mean squared difference or other suitable loss metric. Where available, the loss can incorporate prior knowledge, e.g. if the clinical PET imaging is intended to detect lesions then a phantom with such lesions can be the imaging subject and the loss can quantify a difference in ease with which a lesion is detectable using the transformed first image versus the second image.

The approach leverages available images from a premium imaging system to improve images produced by an entry level imaging system. Advantageously, the neural network is layered atop the existing image acquisition and processing workflow, so that no modification of the existing workflow is required. Further, the training of the neural networks allows for correction of subtle differences that may be difficult to isolate or quantify manually. The images generated by the entry level imaging system implicitly capture all aspects of the imaging workflow and hence embody any deficiencies anywhere in that workflow. Conversely, the images from the premium imaging system implicitly capture a "model" workflow, and hence serve as a suitable training goal for improving image quality.

Although this disclosure describes the PET or hybrid PET/CT imaging systems as illustrative examples, the disclosed approaches may also be applied to any suitable imaging system (e.g., magnetic resonance (MR) imaging systems, functional MR imaging systems, hybrid PET/MR systems, single photon emission computed tomography (SPECT) imaging systems, hybrid SPECT/CT imaging systems, and the like).

With reference to FIG. 1, an illustrative first image acquisition device 12 is configured to acquire imaging data of a subject, and an illustrative second image acquisition device 14 configured to acquire imaging data of a subject. The first and second image acquisition devices 12 and 14 are of the same imaging modality. For example, the first and second image acquisition devices 12 and 14 can be hybrid PET/CT systems, or any other suitable image acquisition device (e.g., MR, hybrid PET/MR, SPECT, hybrid SPECT/CT, and the like). If the goal is to improve the PET images, it is contemplated for one system (most likely the entry level system) to be a standalone PET imaging device while the other system (most likely the premium system) to be a PET/CT imaging device that leverages the CT modality for generating an attenuation map for use in the PET imaging.

The second image acquisition device 14 is not equivalent to the first image acquisition device 12. More particularly, the first image acquisition device 12 is a "lower quality" imaging device as compared to the second image acquisition device 14. That is, the second PET/CT device 14 is configured to acquire the second imaging data as PET images having a higher image quality than the first PET images acquired by the first PET/CT device 12. In one example, the first image acquisition device 12 can be a non-TOF PET imaging device, and the second image acquisition device 14 is a TOF PET imaging device. In another example, the second image acquisition device 14 is a TOF PET imaging device having a second timing resolution, and the first image acquisition device 12 is a TOF PET imaging device having a first timing resolution that is coarser than the second timing resolution. In a further example, the second image acquisition device 14 has a higher spatial resolution than the first image acquisition device 12. As yet another example, suitable for magnetic resonance imaging (MRI) scanners, the first acquisition device may be a lower field (e.g. 0.23 Tesla or 1.5 Tesla) MRI scanner while the second acquisition device may be a higher field (e.g. 3.0 Tesla or higher) MRI scanner.

The first image acquisition device 12 employs a neural network (NN) 16, such as a convolutional NN (or any other suitable NN), which is described further herein. In one embodiment, the NN 16 is an image domain trained neural network. The first image acquisition device 12 also includes a computer or workstation or other electronic data processing device 18 with typical components, such as at least one electronic processor 20, at least one user input device (e.g., a mouse, a keyboard, a trackball, and/or the like) 22, and a display device 24. In some embodiments, the display device 24 can be a separate component from the computer 18.

To produce clinical images for patient diagnosis, therapy monitoring, or other clinical purposes, the at least one electronic processor 20 is programmed to process the imaging data to generate a transformed subject image by reconstructing the imaging data using a first imaging method or process 100 to generate a reconstructed image and then applying the trained NN 16 to the reconstructed image to generate the clinical image. In a variant embodiment (not shown), a trained imaging domain NN is applied to the imaging data before image reconstruction to generate transformed imaging data that is then reconstructed to generate the clinical image. In either case, the display device 24 suitably displays the clinical image.

In a typical contemplated scenario, the first image acquisition device 12 is an entry level imaging device that is owned (or leased, or otherwise procured) by a hospital, clinic, or other medical institution (diagrammatically indicated by an enclosing dashed box 6) with modest resources, e.g. a suburban hospital that is not a trauma center or is a low-level trauma center. By contrast, the second image acquisition device 14 is a premium imaging device that is owned (or leased, or otherwise procured) by a hospital, clinic, or other medical institution with more extensive resources, e.g. a prestigious teaching hospital with substantial ongoing clinical research and associated grant income, a high level regional trauma center, or so forth (diagrammatically indicated by an enclosing dashed box 8). While this is a typical contemplated scenario and is referenced herein as the illustrative embodiment, more generally the first and second acquisition devices are different imaging devices of the same imaging modality with differing capabilities, with the second imaging device being considered "better" in the sense of generating higher quality images of greater clinical efficacy. Moreover, it is contemplated for the first and second imaging devices to be owned (or leased, or otherwise procured) by the same hospital, clinic, or other medical institution.

The training of the NN 16 leverages second training images acquired by the second (e.g. premium) image acquisition device 14 as the "target output" of the NN 16. These second training images are generated by the second image acquisition device 14 using a second imaging method or process 200, which may differ significantly from the first imaging method or process 100 employed at the first (e.g. entry level) image acquisition device 12. For example, in one embodiment the first image imaging method or process 100 employs non-TOF image reconstruction of imaging data acquired by the entry-level image acquisition device 12 which does not provide TOF localization information; while, the second image imaging method or process 200 employs TOF image reconstruction of imaging data acquired by the premium image acquisition device 14 which provides TOF localization information for its detected events. The second imaging method or process 200 may employ more complex image reconstruction, for example implemented on a high speed network server computer 26 available or accessible as part of the extensive resources of the type of medical institution that typically procures a premium TOF PET imaging device. Beyond these technical differences, the two imaging methods or processes 100, 200 may be executed by personnel employing different choices of filters, filter parameters, or so forth.

With continuing reference to FIG. 1, the trained neural network 16 is configured by neural network training to transform first (training) images (i.e., training images) acquired of one or more training subjects by the first image acquisition device 12 into transformed first training images for which a value of a difference metric comparing the transformed first training images and second training images acquired of the (same) one or more training subjects by the second image acquisition device 14 is minimized by the training. It will be appreciated that the term "minimized" does not require a global minimum, (e.g., is sufficient to be produced by an iterative optimization algorithm that operates to adjust weights of the NN to reduce the difference metric, run until a stopping criterion is met, such as iteration-to-iteration change in difference metric value below some threshold, and/or absolute value of difference metric below some threshold, and so forth).

The training of the NN 16 is suitably implemented by an illustrative server computer or other electronic data processing device 28 that implements a neural network trainer 30. In the illustrative embodiment, the server computer 28 and training 30 is owned (or leased, or otherwise procured) by a third entity diagrammatically indicated by an enclosing dashed box 10. This third entity 10 may, for example, be the vendor that sells or leases the imaging devices 12, 14 to the respective medical institutions 6, 8. In this contemplated arrangement, the institution 8 owning the second image acquisition device 14 supplies the second training images to the imaging devices vendor 10 under a purchase contract, or as part of a research and development (R&D) agreement, or so forth. For example, the vendor 10 may contract with the institution 8 owning the second image acquisition device 14 to image a standard set of imaging phantoms (e.g., representing torsos, heads, or other anatomical regions expected to be imaged for various clinical tasks) using their standard clinical imaging protocols embodying the second imaging method or process 200 in order to generate the second training images. The first training images may be acquired of the same set of imaging phantoms by the first image acquisition device 12 during installation of the first image acquisition device 12, or may be acquired well after installation as part of a "retrofit" process in which the image quality-improving NN 16 is added as an additional processing step performed after the standard clinical imaging protocols of the first institution 6 embodying the first imaging method or process 100. This is merely an illustrative example, and other arrangements and associations between the various institutions or entities 6, 8, 10 are contemplated—for example, in another contemplated arrangement, the medical institution 8 that owns the second image acquisition device 14 may also be the entity 10 that performs the NN training 30, e.g. as a service to the medical imaging community at large. (In this case, the two institutions 8, 10 are identical, and the two processing devices 26, 28 may be the same computer server or different computer servers).

The neural network trainer 30 can employ any suitable neural network training algorithm, e.g. employing propagation of errors back through the network (backpropagation) or similar techniques with iterative optimization of the weights of the neural network to minimize (e.g. using gradient descent, Newton's method, or another iterative minimization algorithm) a loss metric quantifying similarity of the first training images transformed by the neural network with the (reference) second training images. The output of the neural network trainer 30 is the trained neural network 16 (for example, stored as a data file storing the neural network topology or a pointer or identifier of that topology along with the optimized weights of the neural network), which is then loaded into the computer 18 for subsequent use in transforming images output by the first imaging method or process 100 into clinical images with improved image quality.

In another embodiment (not shown), the NN is a trained imaging data domain neural network. The trained imaging data domain neural network is configured by neural network training to transform first imaging data (i.e., training imaging data) acquired of one or more training subjects by the first image acquisition device 12 into transformed first training imaging data for which a value of a difference metric comparing the transformed first training imaging data and second training imaging data acquired of the one or more training subjects by the second imaging device is minimized by the training. The operations to train the NN 16 are described in more detail below.

The at least one electronic processor 20, the server computer 26, and/or the server computer 28 are operatively connected with a non-transitory storage medium (not shown) that stores instructions which are readable and executable to perform disclosed operations including performing the first imaging method or process 100 and the second imaging method 200 and to train the NN 16. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the imaging methods or processes 100 or 200 may be performed by cloud processing.

Figure 2:
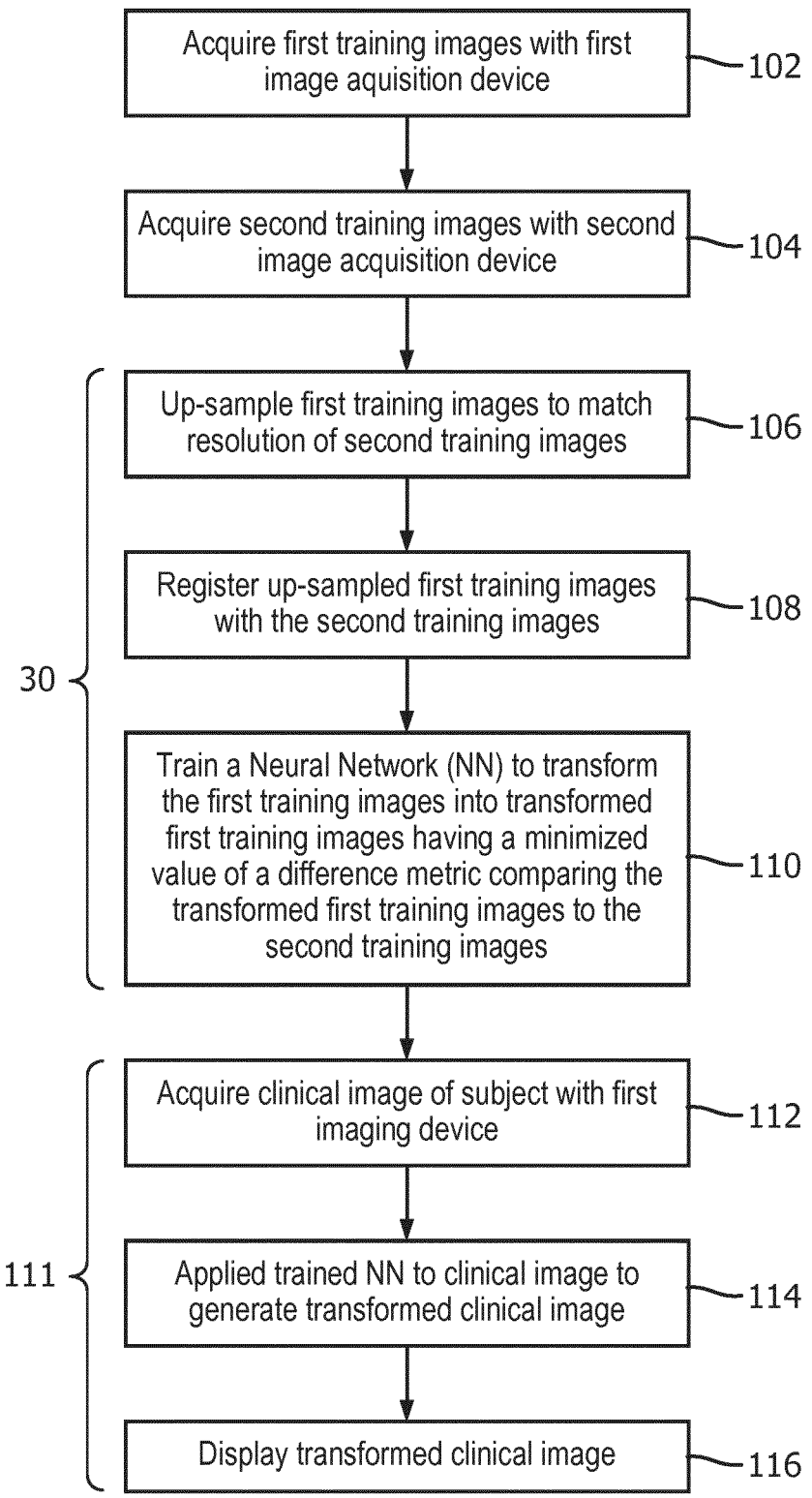
FIG. 2 shows an exemplary flow chart operation of the system of FIG. 1.

With reference to FIG. 2, an illustrative example of the neural network training and the use of the trained neural network 16 to improve the clinical images is diagrammatically shown as a flowchart. At 102, first training images of one or more imaging subjects are acquired using the first image acquisition device 12 (including processing by the first imaging method or process 100 which may include reconstruction of the imaging data, post-reconstruction filtering, and/or so forth).

At 104, second training images of the same one or more imaging subjects as the first training images are acquired using the second image acquisition device 14 (including processing by the second imaging method or process 200 which may include reconstruction of the imaging data, post-reconstruction filtering, and/or so forth). As the same imaging subjects must be imaged in order for the first and second (sets of) training images to be fairly comparable, it is generally expected to be most convenient for the imaging subjects to be one or more imaging phantoms, that is, articles of manufacture constructed to mimic the properties of human organs and tissue and (for PET or SPECT imaging) including reservoirs, assemblies, or absorbent materials for receiving radiopharmaceutical in a manner that mimics radiopharmaceutical administered to a human subject. However, if suitable human subjects are available for imaging at both institutions 6, 8, then the imaging subjects may be actual human imaging subjects. The first and second image acquisition devices 12 and 14 are also of the same imaging modality, again in order for the first and second (sets of) training images to be fairly comparable. In one example, the first image acquisition device 12 and the second image acquisition device 14 are each PET/CT imaging devices. The second PET/CT device 14 is configured to acquire the second training images as PET images having a higher image quality than the first PET training images acquired by the first PET/CT device 12. In another example, the first image acquisition device 12 is a non-TOF PET imaging device, and the acquiring of the first training images includes reconstructing non-TOF PET imaging data acquired by the first image acquisition device to generate the first training images without utilizing TOF localization. The second image acquisition device 14 is a TOF PET imaging device, and the acquiring of the second training images includes reconstructing TOF PET imaging data acquired by the second imaging device utilizing TOF localization.

The neural network training 30 is next implemented by illustrative operations 106, 108, 110 in the illustrative method of FIG. 2. At 106, in some embodiments, the first training images are up-sampled to increase resolution (e.g., a number of pixels or voxels in the image) thereof to match the second training images that may have higher resolution than the first training images. (Step 106 may be omitted if the first and second training images are of the same resolution, or if the neural network 16 incorporates integrated up-sampling).

At 108, the up-sampled first imaging data is spatially registered with the second imaging data. For example, the first and second training images are registered in a common image space.

At 110, the NN 16 is trained to transform the first training images into transformed first training images having a minimized value of a difference metric comparing the transformed first training images and the second training images. The difference metric can be any suitable image comparison metric for comparing the transformed first training images with the second training images, e.g. a pixel-wise difference metric. Since features such as edges are typically important in clinical images, the difference metric may be chosen to emphasize such features, e.g. by first applying an edge detection algorithm to the images and then comparing the edge-transformed images. It is contemplated to employ different difference metrics for training NNs for different clinical applications, depending upon the image characteristics anticipated to be of most value to clinicians. The weights of the NN 16 are adjusted by the training to minimize the value of the difference metric, so that the operation of the trained NN 16 is to transform the first training images to be similar to the second training images. In some examples, the NN 16 is a convolutional NN (CNN). The resulting trained NN 16 is communicated from the server computer 28 to the computer 18 of the first image acquisition device 12 (step not shown in FIG. 2).

With continuing reference to FIG. 2, a set of steps 111 suitably executed at the institution 6 illustrates a suitable application of the trained NN 16. At 112, a clinical image of a clinical subject is acquired with the first imaging device 12 (including processing by the first imaging method or process 100 as in step 102). At 114, the NN 16 produced by the training is applied to the clinical image output by the first imaging method or process 100 to generate a clinical image to be presented to the doctor, oncologist, cardiologist, or other clinician for clinical analysis or use. At 116, the clinical image is displayed on the display device 24. The transformed clinical image may also me saved in a Picture Archiving and Communication System (PACS) or otherwise utilized.

In one illustrative example, the first image acquisition device 12 can be a hybrid PET/CT system, such as a Gemini system, or Ingenuity TF system, (each available from Koninklijke Philips N.V. Eindhoven, the Netherlands) with less than state-of-the-art performance due to crystal properties, timing resolutions, less sophisticated reconstruction and processing algorithms, or other imaging characteristics. The second image acquisition device 14 can be any suitable imaging system that has better performance characteristics than the first image acquisition device 12, such as a Vereos Digital PET (also available from Koninklijke Philips N.V.). With the trained NN 16, the images acquired by the first image acquisition device 12 can be made more comparable to the images acquired by the second image acquisition device 14.

In some examples, the first image acquisition device 12 is a value-based performance LYSO crystal PET system with a Photo-Multiplier Tube readout with about 500-600 picosecond (ps) timing resolution. The second image acquisition device 14 is a Vereos Digital PET system with 325 ps TOF resolution. The NN 16 is trained with imaging data from the Vereos system, and is then applied to the Garnet system so that the Garnet system so that the Garnet system achieves an image quality more similar to TOF Premium PET system.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging method, comprising:
    acquiring first training images of one or more imaging subjects using a first image acquisition device;
    acquiring second training images of the same one or more imaging subjects as the first training images using a second image acquisition device of the same imaging modality as the first imaging device and having a shorter timing resolution than the first imaging device, the first imaging device and the second imaging device being separate imaging devices; and
    training a neural network (NN) to transform the first training images into transformed first training images by:
        comparing the first training images to the second training images; and
        generating the transformed first training images by minimizing a value of a difference metric between the first training images and the second training images.

2. The method of claim 1 further comprising:
    acquiring a clinical image of a clinical subject using the first imaging device;
    applying the NN produced by the training to the clinical image to generate a transformed clinical image; and
    displaying the transformed clinical image.

3. The method of claim 1, further comprising:
    prior to the training, registering the first training images and the second training images in a common image space.

4. The method of claim 3, wherein the second training images have higher resolution than the first training images and the method further includes:
    prior to the registering, up-sampling the first training images to increase resolution thereof to match the second training images; and
    registering the up-sampled first imaging data with the second imaging data.

5. The method of claim 4, wherein:
    the first image acquisition device is a non-time of flight (non-TOF) positron emission tomography (PET) imaging device and the acquiring of the first training images includes reconstructing non TOF PET imaging data acquired by the first image acquisition device to generate the first training images without utilizing TOF localization; and
    the second image acquisition device is a TOF PET imaging device and the acquiring of the second training images includes reconstructing TOF PET imaging data acquired by the second image acquisition device utilizing TOF localization.

6. The method of claim 1, wherein the one or more imaging subjects include at least one of human imaging subjects and imaging phantoms.

7. The method of claim 1, wherein the NN is a convolutional NN (CNN); and
    wherein the first image acquisition device and the second image acquisition device are each positron emission tomography/computed tomography (PET/CT) imaging devices; the second PET/CT device being configured to acquire the second training images as PET images having a higher image quality than the first PET training images acquired by the first PET/CT device.

8. A non-transitory computer-readable medium storing instructions readable and executable by at least one electronic processor to perform an imaging method, the imaging method comprising:
acquiring a subject image of a subject using a first image acquisition device;
applying a trained neural network to the subject image to generate a transformed subject image; and
displaying the transformed subject image;
wherein the trained neural network is configured by neural network training to transform first training images acquired of one or more training subjects by the first image acquisition device or by an equivalent image acquisition device into transformed first training images for which a value of a difference metric comparing the transformed first training images and second training images acquired of the one or more training subjects by a second image acquisition device that is not equivalent to the first imaging device is minimized by the training, the second image acquisition device having a shorter timing resolution than the first imaging device;
wherein the first image acquisition device and the equivalent image acquisition device are of a common device model with a common imaging configuration; and
the second image acquisition device is not equivalent to the first image acquisition device at least in that:
the second image acquisition device is a time-of-flight (TOF) positron emission tomography (PET) imaging device and the second training images are TOF PET training images, and
the first image acquisition device is a non TOF PET imaging device and the first training images are non TOF images and the subject image is a non TOF image.

9. The non-transitory computer-readable medium of claim 8, wherein the first training images are acquired by the first image acquisition device.

10. The non-transitory computer-readable medium of claim 8, wherein the second image acquisition device is not equivalent to the first image acquisition device further in that the second image acquisition device which is a TOF PET imaging device has a higher spatial resolution than the first image acquisition device which is a non TOF PET imaging device and the second training images have higher spatial resolution than the first training images and the second training images have higher spatial resolution than the subject image.

11. The non-transitory computer-readable medium of claim 10, wherein the trained neural network is a trained convolutional neural network.

12. An imaging system, comprising:
a first image acquisition device configured to acquire imaging data of a subject;
at least one electronic processor programmed to:
process the imaging data to generate a transformed subject image by one of (i) reconstructing the imaging data to generate a reconstructed image and applying an image domain trained neural network to the reconstructed image or (ii) applying a trained imaging data domain neural network to the imaging data to generate transformed imaging data and reconstructing the transformed imaging data; and
control a display device to display the transformed subject image;
wherein one of:
(ia) the trained image domain neural network is configured by neural network training to transform first training images acquired of one or more training subjects by the first image acquisition device into transformed first training images for which a value of a difference metric comparing the transformed first training images and second training images acquired of the one or more training subjects by a second image acquisition device is minimized by the training, or (iia) the trained imaging data domain neural network is configured by neural network training to transform first training imaging data acquired of one or more training subjects by the first image acquisition device into transformed first training imaging data for which a value of a difference metric comparing the transformed first training imaging data and second training imaging data acquired of the one or more training subjects by the second imaging device is minimized by the training, the second image acquisition device having a shorter timing resolution than the first imaging device
wherein the first image acquisition device and the equivalent image acquisition device are of a common device model with a common imaging configuration; and
wherein the second image acquisition device is not equivalent to the first image acquisition device al least in that:
the second image acquisition device is a time-of-flight (TOF) positron emission tomography (PET) imaging device having a second timing resolution, and
the first image acquisition device is a TOF PET imaging device having a first timing resolution that is coarser than the second timing resolution.

13. The imaging system of claim 12, wherein the trained image domain neural network is configured by neural network training to transform first training images acquired of one or more training subjects by the first image acquisition device into transformed first training images for which a value of a difference metric comparing the transformed first training images and second training images acquired of the one or more training subjects by the second image acquisition device is minimized by the training.

14. The imaging system of claim 12, wherein the trained imaging data domain neural network is configured by neural network training to transform first training imaging data acquired of one or more training subjects by the first imaging device into transformed first training imaging data for which a value of a difference metric comparing the transformed first training imaging data and second training imaging data acquired of the one or more training subjects by the second image acquisition device is minimized by the training.

15. The imaging system of claim 12 wherein the second image acquisition device has a higher spatial resolution than the first image acquisition device.

* * * * *